United States Patent [19]

Cohen

[11] Patent Number: 4,899,732
[45] Date of Patent: Feb. 13, 1990

[54] MINISCOPE

[75] Inventor: Donald M. Cohen, Irvine, Calif.

[73] Assignee: Baxter International, Inc., Deerfield, Ill.

[21] Appl. No.: 240,032

[22] Filed: Sep. 2, 1988

[51] Int. Cl.$^4$ .............................................. A61B 1/06
[52] U.S. Cl. ...................................................... 128/6
[58] Field of Search ......................................... 128/4, 6

[56] References Cited

U.S. PATENT DOCUMENTS 3,521,620  7/1970  Cook et al. ........................... 128/772
4,736,733  4/1988  Adair ....................................... 128/6

FOREIGN PATENT DOCUMENTS 0176865  9/1985  European Pat. Off. .
8701600  9/1985  European Pat. Off. .
0254885  6/1987  European Pat. Off. .

Primary Examiner—William H. Grieb
Attorney, Agent, or Firm—Michael C. Schiffer; Sandra S. Schultz

[57] ABSTRACT

A miniscope catheter which is constructed to allow the operator to control the deflection of the catheter tip. The catheter miniscope of the invention includes a catheter body having at least one lumen. An optical filament is positioned through this lumen and is secured to the catheter at a location proximate the catheter distal end. In order to provide for the deflection of the catheter tip portion the catheter miniscope further includes a means which can be operated to apply a force against said optical filament to longitudinally drive the optical filament in at least a first direction within the lumen. This longitudinal movement of the optical filament causes a bending moment in the catheter tip to deflect the tip. By providing that the optical filament can be longitudinal moved in opposite longitudinal directions the catheter distal tip can be made to deflect in two opposing directions.

31 Claims, 1 Drawing Sheet

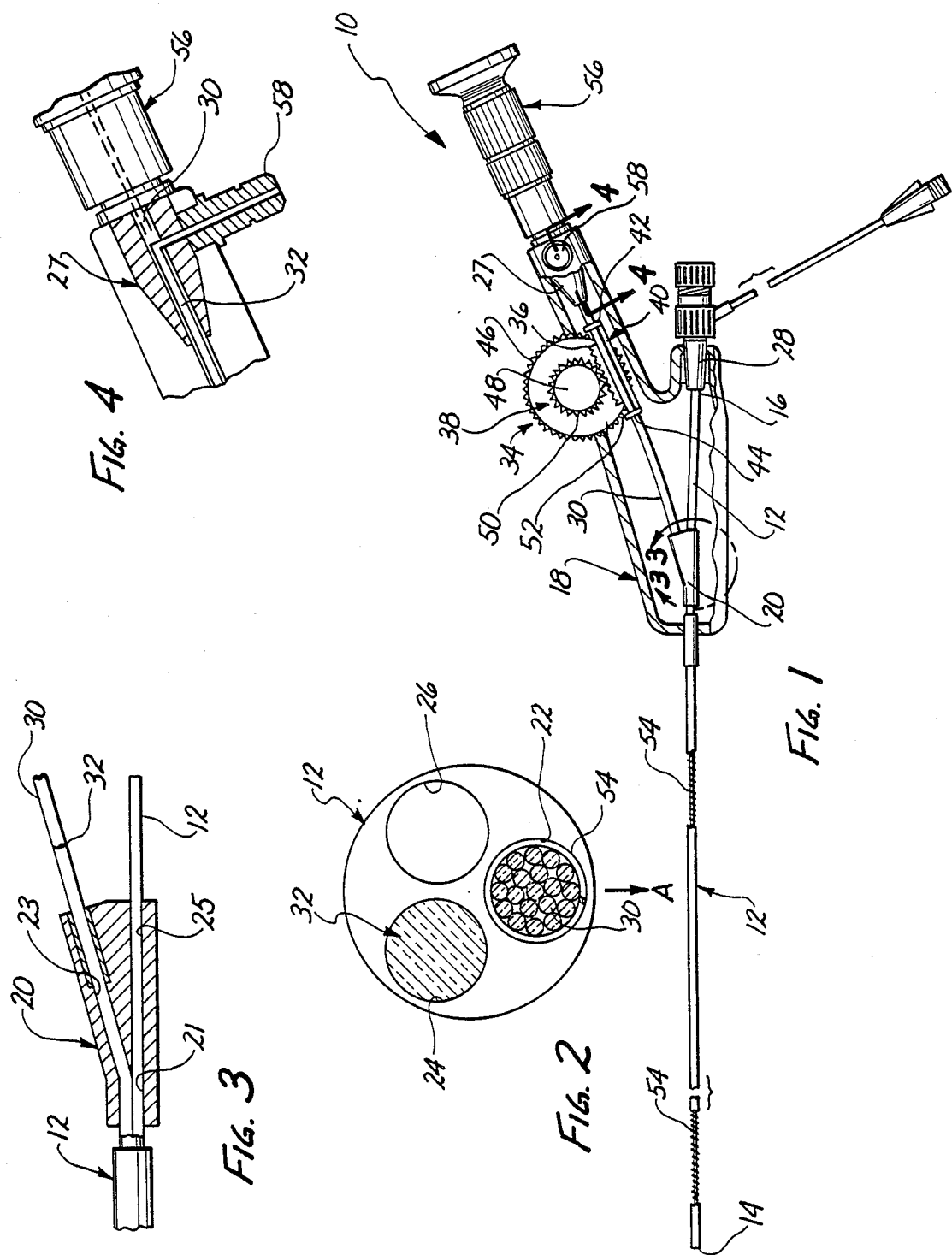

MINISCOPE

BACKGROUND OF THE INVENTION

The present invention is directed to catheters, and particularly to steerable, miniscope catheters.

The use of miniscopes for performing diagnostic testing and for assisting in the performance of certain types of surgery is gaining acceptance in the field of medicine. Miniscopes are advantageously utilized in procedures requiring passage through very small ducts or passageways of the patient. Examples of such procedures include the examination of the bile and pancreatic ducts, with reference being made to "Direct Cholangioscopy and Pancreatoscopy at Time of Endoscopic Retrograde Cholangiopancreatography", Richard A. Kozarek, M.D., The American Journal of Gastroenterology, Vol. 83, No. 1, 1988, pages 55–57, and "Endoscopy of the Gallbladder as Control of Gallstone Therapy with Methyl-tert-Butyl Ether", Leuschner, Helstern, Birkenfeld, Leuschner, Gatzen, Kurtz and Fischer, The American Journal of Gastroenterology, Vol. 83, No. 2, 1988, pages 169–172.

While the use of miniscopes is increasing in diagnostic and surgical procedures, such devices suffer intrinsic disadvantages. Basically a miniscope is a multiple lumen catheter equipped with one or more optical filaments, which filaments may consist of a single fiber or a coherent bundle of optical fibers. The filament is positioned within a selected one of the catheter lumens. The optical filament used in constructing the catheter miniscopes are selected from specific types of optical filament. For example, the catheter miniscope will include at least one optical filament, typically a coherent bundle of glass fibers which possesses sufficient light transmissive properties, and while providing minimal distortion, to function as the view scope. This optical filament has a lens fitted at its distal end, that is the end which will lead the catheter into the body. This lens will be sufficient enough to magnify and focus the viewed object. A viewing eye piece will be secured at the opposite, proximal end of this filament optic. Additional optical filaments can be included for providing illumination. These types of optical filaments need not possess the same optical purity as the optical filament used to function as the viewing filament.

Generally miniscopes must have a relatively narrow diameter in order to allow access into the small conduits for which such devices are intended. For example, miniscope catheters having an outside diameter of seven french or less would be desirable for atraumatic passage into the bite or pancreatic ducts. While catheter miniscopes having this diameter or less have been constructed, such catheter miniscopes do not possess the type of maneuverability required to manipulate the catheter distal end carrying the catheter optics. This is particularly critical when the catheter needs to be moved into a particular duct, which intersects another duct. Specifically, the distal end of the catheter must be deflectable to provide the doctor with sufficient enough control to insert the catheter into the proper duct.

Catheters possessing the desired maneuverability do exist. Such catheters rely upon different techniques for providing the desired maneuverability. Basically, the maneuverability of the catheter is provided by bending the distal tip of the catheter. This allows the catheter to be maneuvered through tortuous passages of the patient's body during a procedure. One type of mechanism for bending the catheter tip involves pre-forming the distal tip to the desired shape of the passage through which the catheter will be positioned. While this is somewhat effective for certain procedures, such types of catheters can not be satisfactorily controlled due to the lack of torque transmission over the length of the catheter body. Another technique involves inserting a stylet into a catheter lumen, with the stylet being preformed. This type of procedure suffers the same disadvantage as preforming the catheter distal end.

An early device for truly controlling the maneuverability of catheter distal ends is taught in U.S. Pat. No. 3,521,620, issued to Cook on July 28, 1970. The taught device is basically a coil spring which is fitted about a wire. This wire is eccentrically secured to the distal end of the coil spring. The wire turnings at the distal end of the coil spring are spatially separated, while the remainder of the coil spring is tightly wound. When the wire is pulled the coil distal end windings become compressed on one side. The eccentric attachment of the wire to the coil distal end causes a bending moment which differentially compresses the coil windings. The result is an off axis deflection of the coil. This device can be inserted into a lumen of a catheter. The off axis deflection of the coil is transmitted to the distal end of the catheter, resulting in a deflection of the catheter distal tip.

A similar approach for controlling the deflection of a catheter distal end is taught in European Patent Applications 176,865, published on Sept. 4, 1986, and 254,885, published on March 2, 1988. The catheters taught in these two published applications cause the distal tip deflection by applying tension to a wire which has been secured eccentrically at the distal end of the catheter.

Other approaches for controlling the deflection of a catheter distal end involve inflating an eccentric catheter balloon, which has been constructed in the distal end. Some catheters may utilize short bursts of gas from out of a side vent to deflect the catheter distal end.

Some techniques involve the construction of the catheter wall at the distal end with portions of differing rigidity, e.g. by varying the thickness of the wall about the catheter circumference. This may also be accomplished by affixing a rigid member along a portion of the catheter wall. When the distal end is subjected to an axial compressive force the rigid portion will not as easily constrict. This results in the catheter bending towards the less rigid, or thinner portion of the side wall. An example of this type of catheter is disclosed in the Patent Cooperation Treaty Patent Application Number WO 87/01600, which was published on March 26, 1987.

While all of the approaches taught by these references provide for adequate control of the distal end deflection, such approaches are unavailable for the catheter miniscope. This is because such catheter miniscopes must possess a relatively small outside diameter, e.g. 2.8 millimeters or less. The methods employed in the above referenced disclosures require more space than is available with catheters of this size, particularly, when such catheters must also include at least one working lumen. The working lumen would have to be provided with a sufficient size to accommodate the passage of guide wires, electrical wiring or fluid. The space availability is also compromised by the fact that such catheter miniscopes will be provided with the necessary optical filaments.

There thus exists the need to construct a catheter miniscope having the necessary optical filaments, while also being designed to provide the necessary maneuverability to deflect the distal end.

SUMMARY OF THE INVENTION

The present invention overcomes the above disadvantages by providing a miniscope catheter which is constructed to allow the operator to control the deflection of the catheter tip. The catheter miniscope of the invention includes a catheter body having at least one lumen. At least one optical filament, which may either be an individual fiber of a bundle of optical fibers, is positioned through this lumen and eccentrically secured to the catheter at the catheter distal end. In order to provide for the deflection of the catheter tip portion the catheter miniscope further includes a means which can be operated to apply a force against the optical filament to longitudinally advance or retract the optical filament along the long catheter axis. This longitudinally movement of the optical filament causes a bending moment in the catheter tip, attributable to the eccentric securing of the optical filament, which deflects the tip portion. This longitudinal advancement or retraction of the optical filament provides the ability of deflecting the catheter distal end in at least two opposing directions.

Specifically, the present invention is directed to a catheter having a catheter body with at least three lumens. A first optical filament formed from a bundle of fused glass fibers is positioned in one of the lumens and eccentrically secured to the catheter at a location proximate the catheter distal end. The mechanism for driving the optical filament is positioned in a handle into which the proximal end of the catheter is fitted. This mechanism can be operated to apply the force against the optical filament to either advance or retract this filament longitudinally through the catheter.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a side, partially sectioned view of a miniscope catheter in accordance with an embodiment of the invention., FIG. 2 is an end on view of the distal end of the catheter portion of the catheter miniscope of FIG. 1;

FIG. 3 is an enlarged, cross-sectional view of the circled portion of FIG. 1 along lines 3—3; and FIG. 4 is an enlarged, cross-sectional view of the circled portion of FIG. 1 along lines 4—4.

DESCRIPTION OF THE PREFERRED EMBODIMENTS

The present invention is directed to a miniscope catheter, typically having a catheter body of less than 2.8 millimeters in outer diameter. Miniscopes having such dimensions would be useful in performing diagnostic procedures by the insertion of the catheter miniscope into the smaller body ducts not presently accessible with available scopes. Furthermore, the miniscopes of the invention may be inserted through working lumens of larger endoscopes. The miniscopes of the invention may also be formed with at least one working lumen, i.e. a non-obstructed lumen. Fluids may be directed to desired body parts through this working lumen.

In one particular example, the miniscope of the invention can be used to view the interior of the gall bladder. This is possible because of the small outer diameter of the catheter body which can fit into the bile duct without the necessity of performing a sphincteromtomy. The viewing capabilities of the miniscope allow a surgeon to examine the inside of the bile ducts and the gall bladder. Furthermore, if so desired a liquid, e.g. a contrast medium, can be directed through the catheter working lumen into the bile duct or gall bladder. The catheter miniscopes of the invention are useful for many other types of diagnostic or surgical procedures.

In order to enhance the useability of the miniscope catheter of the invention, the distal tip portion of the catheter must be steerable. This is provided by constructing the catheter miniscope with the function of deflecting the distal tip portion in at least a first direction away from the longitudinal axis of the catheter. In this manner the surgeon operating the catheter miniscope merely selectively deflects the distal tip to steer the catheter miniscope in at least one direction. Preferably the catheter miniscope is constructed to provide for deflection of the catheter distal tip in two or more opposing directions. This further enhances the ability to steer the catheter miniscope of the invention.

Referring now to FIG. 1, a catheter miniscope in accordance with one embodiment of the invention is seen generally at 10. The miniscope 10 includes a catheter body 12, which has a distal end 14 and a proximal end 16, and handle 18. The proximal end 16 of the catheter body 12 is partially positioned within the handle 18. A Y-intersection connector 20 is fitted to the catheter body 12, which connector 20 is fitted within the handle 18.

The connector 20 is formed with a Y-shaped internal passageway, illustrated in FIG. 3 at 21, for receiving the catheter body 12. As will be described more fully herein, this passageway 21 is formed to allow for the passage of the viewing and illumination optical filaments through one arm 23 of the passageway 21, while the remainder of the catheter passes down the other arm 25 of the passageway 21.

The catheter 12 is formed by conventional procedures, e.g. by extruding a suitable polymer, e.g. polyvinylchloride, through an appropriately configured die to form one or more lumens. As stated, the present invention will be described in relation to a catheter body having three lumens, with the die used to form the catheter body 12 having the appropriate configuration to form such a catheter body 12. The precise method of forming such a catheter body 12 is not critical for the instant invention, and will thus not be described in any detail herein. In this regard, any conventional technique for forming catheters can be used to manufacture the catheter body 12.

The handle 18 is a generally hollow structure formed to receive the catheter body 12, connector 20 and the mechanism for applying force against an optical filament and an optical eyepiece, both of which will be described more fully herein. The precise construction and shape of the handle 18 is not critical to the invention, however, in accordance with the preferred illustrated embodiment of the miniscope 10 the handle 18 is formed to be easily received within the hand of the operator of the miniscope 10, and to allow for easy access to the various operating components, e.g. the drive mechanism and eyepiece, of the miniscope 10.

The miniscope 10 further includes various optical filaments, which for the purpose of the present invention shall include individual fibers or a bundle of fibers. These filaments, seen generally at 30 and 32, are selectively positioned in individual ones of the lumens of the catheter body 12, as illustrated lumens 22 and 24. The optical filament 30 will function as the viewing filament, while the filament 32 will function as the illumination filament.

Filaments which can be used in the practice of the invention are those which have the characteristic of total internal reflection and low optical attenuation. In this regard, such filaments are typically formed with an internal core surrounded by a cladding, with the cladding formed from a material having a lower index of refraction. When such filaments are a bundle of individual fibers, such fibers are also formed with an internal core surrounded by a cladding of a material having a lower index of refraction. In accordance with the preferred embodiment, the individual fibers are fused together by the fusing of the material forming the outer cladding.

The precise materials from which the optical filaments are formed, and the geometric shape of such filaments are not critical to the invention so long as such materials and geometry provide the filaments with the desired optical characteristics. These optical characteristics will be dependent upon whether the filament is to function as the viewing or illumination filament 30 or 32.

In accordance with a preferred embodiment, the viewing filament 30 will have to be an optical filament having good light transmissive characteristics, as depicted by an attenuation diagram, in addition to the image preservation characteristics. The illumination filament should possess a numerical aperture, or cone of acceptance selected to provide illumination of the entire viewing field, which in the preferred embodiment will have an angle of view of about 60°. This should correspond to a numerical aperture of at least 0.50. The illumination filament should also display an attenuation below 1 dB/m in the visible range (400 to 700 nm).

In accordance with a more preferred embodiment of the invention, the optical filament selected for the viewing filament 30 is formed from glass, and even more preferably is a filament formed from a bundle of coherent glass filaments, which are preferably fused together. The illumination filament 32 may also be a glass fiber or bundle of glass fibers. However, it is typically more desireable to use a polymeric optical filament for the illumination filament 32, generally a filament formed with an inner core surrounded by another polymer having a refractive index less than the refractive index of the material forming the core. Typical polymeric optical filaments are formed from a polyacrylic material core coated with a fluorinated polymer cladding. The elastic moduli of such filaments are considerably smaller than analogous glass filaments. Accordingly, catheters employing plastic illumination filaments will be substantially less stiff than those employing glass illumination filaments.

As stated, the connector 20 is fixed to the catheter body 12, with the optical filaments being passed down the arm 23 of the passageway 21, with the remainder of the catheter body 12 passing down the arm 25. That is, the optical filaments 30 and 32 are removed from the lumens 22 and 24 by cutting open the respective lumens 22 and 24 of the catheter body 12. The filaments 30 and 32 are then drawn through the arm 23, while the catheter body 12 is drawn through the arm 25. The catheter body 12 is fixed in the connector 20 by suitable means, e.g. an adhesive.

The exposed ends of the optical filaments 30 and 32 are fixed in an eyepiece coupler 27. This eyepiece coupler 27 includes two passages, not shown, for individually receiving the viewing filament 30 and the illumination filament 32. The passage for the viewing filament 30 will generally extend out the end of the coupler 27, while the passage for the illumination filament 32 will extend laterally through the wall of the coupler 27. The illumination filament 32 will be exposed to the exterior of the coupler 27 through this passage. In this regard, reference is made to FIG. 4 which illustrates a portion of the handle 18 in which the eyepiece coupler 27 is mounted. As seen, a light socket 58 extends laterally out from a hole, not shown, formed in the side of the handle 18. This light socket 58 is integrally formed out from the side of the coupler 27, and includes the passage through which the illumination filament 32 is passed. The exposed end of the illumination filament 32 is illuminated by any suitable source, seen generally at 60, with the preferred embodiment being a light source 60 which includes a mechanism for coupling to the light socket 58.

The viewing filament 30 will extend out of the coupler 27 and be fitted to an eyepiece 56. The eyepiece 56 may be any suitable eyepiece. e.g. that eyepiece used in an ureterscope manufactured by the Baxter Healthcare Corporation, a Delaware Corporation residing in Deerfield, Illinois, which eyepiece used in such ureterscope has a Model number GU-77. The manner in which the viewing filament 30 is connected in the eyepiece 56 is not critical to the invention, and will not be discussed any further herein.

While either the viewing or illumination filaments may be used to exert the deflection force on the distal tip of the catheter, in accordance with the preferred embodiment, the viewing filament 30 will be used. In this regard, the viewing filament 30 is fixed to the catheter body 12 at a location contiguous to the catheter distal end 14. The securing of the filament 30 at the distal end 14 is generally performed by an adhesive. As stated, the opposite end of the filament 30 is fixed in the eyepiece 56. A portion of the filament 30 positioned inside the handle housing 18 is connected to a mechanism, seen generally at 34, which can be operated to either pull the filament away from or push it towards the distal end 14. When the filament 30 is pushed towards the distal end 14, a load is applied to the filament as a compression force, while the load applied to the filament 30 when it is pulled away from the distal end 14 is a tensile force. This load is transferred to the distal end 14, and in particular to the point of the catheter body 12 to which the filament 30 is secured, which causes the deflection of this end 14.

In order to prevent dislodging of the viewing filament from the eye piece 56 a sufficient amount of slack of the viewing filament 30 is positioned in the interior of the handle 18. That is, a sufficient length of the viewing filament is provided in the handle housing 18 to prevent the dislodging of the illumination filament from the eye piece 56 upon applying a load to the viewing filament by the mechanism 34.

The direction of the deflection will depend upon whether the filament 30 is being subjected to a compressive or tensile load. Furthermore, the direction of the deflection will be dependent upon the construction of the catheter, and whether such catheter body 12 is reinforced in any manner. As seen in FIG. 2, that lumen 22 in which the viewing filament 30 is positioned is located off center, or to the side of the catheter body 12 axis. When the viewing filament 30 is subjected to a tensile force by pulling upon the filament a differential compression of the catheter will occur. Thus the deflection upon pulling the viewing filament 30 will occur in the direction indicated by the arrow A. Applying a compressive force upon the filament by pushing upon the same will cause the catheter body 12 to be deflected in the opposite direction.

The preferred mechanism 34, which is illustrated in FIG. 1, for applying the tensile and compressive force upon the viewing filament 30 is a rack and pinion arrangement. A rack 36 is mounted to the filament 30, and a pinion 38 is mounted for rotation within the handle 18. More specifically, the rack 36 is secured to the filament 30 near its proximal end, that is the end connected to the eyepiece 56. The rack 36 can be affixed to the filament 30 by any suitable method, e.g. adhesion. The rack 36 and filament 30 are mounted for a sliding relationship within a frame 40. This frame 40 includes two arms 42 and 44 which are formed with cut-outs through which the combination of the rack 36 and filament 30 are slidably received.

The pinion 38 is connected to a thumb wheel 46 by any suitable mechanism for transferring the rotational force of the thumb wheel 46 to the pinion 3B. In accordance with the illustrated embodiment the pinion 38 and thumb wheel 46 are mounted together about a shaft 48. Thus the rotation of the thumb wheel 46 simultaneously rotates the pinion 38. However, the pinion 38 and thumb wheel 46 can be mounted to rotate upon two different shafts, not shown, which are mounted in the handle housing 18. The shaft about which the thumb wheel 46 is mounted can be coupled to the shaft about which the pinion 38 is mounted by suitable means, e.g. pulleys or gears. This arrangement would effect the transfer of the rotation of the thumb wheel shaft to the pinion shaft by the pulleys or gears.

The pinion 38 is formed with a series of teeth about its periphery, as seen generally at 50. These teeth 50 mate with a series of teeth formed on the opposing surface of the rack 36, with such teeth seen generally at 52. By rotating the pinion 38, through the operation of the wheel 46, the teeth 50 engage and travel along the series of the teeth 52. The operation of the rack and pinion mechanism 34 applies a load to the filament 30. Depending upon the direction at which this load is applied the filament 30 is subjected to a tensile or compressive load.

Since the filament 30 will be subjected to a load by the operation of the rack and pinion mechanism 34, it is necessary for such a filament to possess sufficient strength to resist breakage. It has been found that the minimum ultimate strength of a useful filament, that is a filament possessing the necessary optical characteristics, is at least about seven thousand pounds per square inch (psi). By "ultimate strength" it is meant the stress at which the ultimate failure (breakage) of the filament occurs. Furthermore, while mechanism 34 may apply the force to a plastic filament, it has been found that the most preferred filament is a glass filament. The glass filament will not plastically distort as easily as a polymeric filament, and thus not suffer as much distortion in light transmission characteristics. Generally, in glass filament the difference between the elasticity of the materials forming the filament core and the cladding is closer than with plastic filaments. Thus the application of a load to the glass filament will not as likely cause a separation between the cladding and the core as will occur with the plastic filaments.

An even more preferred embodiment is the use of a bundle of fused glass fibers as that filament to which the load is applied by the mechanism 34. An unfused bundle of glass fibers was found to have an uneven distribution of stress when load was applied in comparison to a bundle of fused fibers. As a result, a few of the individual fibers of the bundle carried an inordinate proportion of the load, and would easily break. This would result in a distortion of the light transmission characteristics of the viewing bundle fiber 30.

In order to promote the direction of deflection of the distal end 14 the catheter miniscope 10 can include a stiffening element. This stiffening element, seen generally in phantom at 54, will provide for different regions of stiffness about the viewing filament 30. The stiffer regions will only bend, or deflect at a higher load. Thus by the appropriate positioning of the different regions of stiffness, the positioning of the deflection is controlled to the desired location along the catheter body 12. Since it is usually desireable to provide for the most deflection at the distal end 14, it is the region at this location which has the least degree of stiffness. Conversely, the remaining regions are more stiff.

While any suitable structure can function as the stiffening element 54, preferably the stiffening element 54 is a wire coil, or metal spring, through which is positioned the viewing filament 30. The different regions of stiffness are provided by manipulating the spacing between adjacent windings of the coil. The normal spring windings are closely wound. At those locations at which the overall stiffness is to be lessened, these windings are moved apart. Thus the spring at these locations will more easily bend in response to a tensile load in the filament, that is become compressed, and thus allow for a greater degree of deflection.

In this regard, reference is made to the teachings of U.S. Pat. No. 3,521,620, issued to Cook on July 28, 1970, pertaining to physical arrangement of the coil spring. In particular, reference is made to the spatial separation of the distal end coil windings, and the effect of this separation when the spring is subjected to a compressive force. Accordingly, these teachings are incorporated herein by reference.

While the manipulation of the coil spring 54 is usually provided at the distal end 14, it should be noted that such manipulation may also be provided at a mid-point along the spring 54, or even at different locations along the spring 54. Furthermore, while the invention is being described and illustrated as using a spring 54 as the stiffening element, other embodiments are also envisioned. For example, the catheter body 12 can be formed with a wire mesh, or similar material, wrapped about the body up to a predetermined location from the distal end 14. This will provide the catheter body 12 with one region of stiffness along which the wire mesh is situated, with a second, lesser region of stiffness at the distal end. The method of winding a wire mesh about a catheter body is known and not critical to the invention.

It may also be suitable to form the catheter body 12 from two types of polymeric material. That is, a body section can be formed from a relatively rigid polymeric material, while a tip portion can be formed from a soft polymeric material. This will provide for the two regions of differing stiffness. The methods of fabricating such types of catheters are well known in the art and not critical to the invention.

While the described and illustrated embodiment uses only a single optical filament for causing the deflecting of the catheter distal end 14, it should be noted that more than one optical filament can be used for the same purpose. In this regard, a second mechanism, e.g. rack and pinion mechanism 34 is included in the handle 18, with the second rack affixed to the other optical filament, i.e. illumination filament 32. If such an embodiment is desired, than the optical filament used for illumination filament 32 should be able to bear a tensile load of at least two pounds. Typically sized filaments which are useful for the practice of the invention, that are those filaments which are small enough to fit within the described catheter body 12, should have a minimum strength of at least seven thousand psi. Greater safety can be achieved by using an even larger filament, however the overall size constraints of the catheter body 12 must be followed in order to provide a miniscope with the desired outer diameter. Furthermore, a bundle of fused glass filaments may be used as the illumination filament 32, with this filament being used alone or in combination with the viewing filament 30 to cause deflection of the catheter distal end 14.

While the preferred embodiments have been described, various modifications and substitutions may be made thereto without departing from the scope of the invention. Accordingly, it is to be understood that the invention has been described by way of illustration and not limitation.

What is claimed is:

1. A miniscope catheter comprising:
   a cylindrical body formed with a distal and proximal end and at least a first lumen traversing through said body;
   at least a first optical filament positioned in one of said lumens and eccentrically secured to said body at a region to be deflected;
   viewing means associated with the proximal end of said cylindrical body for viewing images through said first lumen of said body; and
   means associated with said body which can be operated to apply a force against said optical filament to longitudinally drive said optical filament in at least a first direction within said lumen.

2. The miniscope of claim 1 wherein said optical filament possess sufficient ultimate strength to resist breakage when said force is applied.

3. The miniscope of claim 1 wherein said filament is eccentrically positioned in said cylindrical body and secured proximate said distal end to promote deflection of the distal end.

4. The miniscope of claim 3 and wherein said viewing means is associated with that end of said first optical filament opposite said end secured to said body which is formed for viewing images through said filament.

5. The miniscope of claim 4 and wherein said cylindrical body includes a second lumen, and said miniscope includes a second optical filament having a proximal and a distal end which passes through said second lumen, and illumination means associated with the proximal end of said second optical element for illuminating the region to be viewed.

6. The miniscope of claim 3 wherein said cylindrical body includes a second lumen, and said miniscope includes a second optical filament having a proximal and distal end and passes through said second lumen and said viewing means is associated with the proximal end of said second optical filament for viewing images through said filament.

7. The miniscope of claim 6 and wherein said scope includes illumination means associated with the proximal end of said first optical element for illuminating the region to be viewed.

8. The miniscope of claim 3 wherein said force applying means is formed to engage said optical filament surface and apply a force to drive said filament in said first longitudinal direction.

9. The miniscope of claim 3 wherein said force applying means is operable for applying a force to said filament to drive said filament in two opposing longitudinal directions.

10. The miniscope of claim 3 wherein said force applying means is formed to engage said optical filament surface and apply a force to drive said filament in two opposing longitudinal directions.

11. The miniscope of claim 10 further including a handle formed with a cavity, said cylindrical body proximal end being positioned in said handle cavity with said first filament having an end exposed in said cavity.

12. The miniscope of claim 11 wherein said force applying means includes a first structure mounted to said filament and a second structure mounted selectively operable for movement in two opposing directions in said handle, said second structure being formed to engage a surface of said first structure to move said first structure and said filament one of said two opposing longitudinal directions when said second structure is being operated to be moved in one of said two opposing directions.

13. The miniscope of claim 12 further including a means for limiting the longitudinal movement of said filament in either of said opposing directions.

14. The miniscope of claim 12 wherein said first structure is a rack which is secured to said filament positioned in said handle, said rack having at least a first surface formed with teeth, and wherein said second structure is a pinion which is formed with a circumferential surface having teeth, said pinion being mounted for rotation in said handle in a position proximate to said rack to place said pinion teeth into engagement with at least some of said teeth of said rack first surface.

15. The miniscope of claim 14 further including a wheel mounted for rotation in said handle, said wheel being mounted to allow access outside said handle, said wheel being secured to said pinion to rotate said pinion as it is rotated.

16. The miniscope of claim 14 further including a wheel mounted for rotation in said handle, said wheel being mounted to allow for access outside said handle, said wheel being coupled to said pinion to rotate said pinion as it is rotated through a gear assembly.

17. The miniscope of claim 14 further including a wheel mounted for rotation in said handle, said wheel being mounted to allow for access outside said handle, said wheel being coupled to said pinion to rotate said pinion as it is rotated through a pulley assembly.

18. The miniscope of claim 11 further including a means for limiting the longitudinal movement of said filament in either of said opposing directions.

19. The miniscope of claim 18 wherein said optical filament possess sufficient ultimate strength to resist breakage when said force is applied.

20. The miniscope of claim 19 further including at least one more lumen traversing through said body, with at least one additional filament being positioned in said lumen.

21. The miniscope of claim 19 further including at least two more lumens traversing through said body, with at least one additional filament being positioned in one of said lumens.

22. The miniscope of claim 21 further including a second drive means for driving said additional filament two opposing directions.

23. The miniscope of claim 21 wherein said lumen in which said first filament is positioned is formed eccentrically in said body.

24. The miniscope of claim 23 further including a means positioned about said first filament which is formed with a first region of low rigidity located along said filament proximate to said body distal end, and a second region of high rigidity located over the remainder of said filament.

25. The miniscope of claim 23 further including a coil spring positioned about said first filament within said lumen, said coil spring being formed with its coils located about said filament proximate to said body distal end being spatially separated, while the remainder of said coil spring is tightly wound.

26. The miniscope of claim 23 wherein said body is formed with a main body section prepared from a rigid polymeric material and a tip section prepared from a soft, pliable polymeric material.

27. The miniscope of claim 23 wherein said first filament is characterized by having an ultimate strength of at least seven thousand pounds per square inch.

28. The miniscope of claim 23 wherein said cylindrical body is formed with an outer diameter no greater than 2.8 millimeters.

29. A miniscope according to claim 1 and wherein the viewing means is an eyepiece means having a lens to allow direct visual observation through the lumen.

30. A catheter miniscope comprising:
a catheter body having a distal and proximal end and an outer diameter of no greater than 2.8 millimeters, said body being formed with at least three eccentrically positioned lumens;
a first optical filament formed from a fused bundle of individual glass filaments positioned in one of said lumens and secured in said lumen at a location proximate said catheter body distal end;
a second optical filament positioned through another of said lumens;
a handle means which is formed with a cavity for receiving a portion of said catheter body proximal end;
said first and second optical filaments being formed with exposed ends positioned in said handle cavity, said second optical filament exposed and being positioned to receive light;
an eyepiece means coupled to said exposed end of said first optical filament, said eyepiece means being formed with lens to allow visual observation through said first optical filament, said eyepiece means being secured to said handle means; and
a means located in said housing which is formed to engage said first optical filament surface and apply a force for driving said filament in two opposing longitudinal directions whereby the distal end of said catheter is deflected.

31. A catheter miniscope comprising:
a catheter body having a distal and proximal end and an outer diameter of no greater than 2.8 millimeters, said body being formed with at least three eccentrically positioned lumens;
a first optical filament formed from a fused bundle of individual glass filaments positioned in one of said lumens;
a second optical filament positioned through another of said lumens and secured thereto at a region proximate the distal end of the catheter body;
handle means which is formed with a cavity for receiving a portion of said catheter body proximal end;
said first and second optical filaments being formed with exposed ends positioned in said handle cavity, said second optical filament exposed end being positioned to receive light;
an eyepiece means coupled to said exposed end of said first optical filament, said eyepiece means being formed with lens to allow visual observation through said first optical filament, said eyepiece means being secured to said handle means; and
means for engaging said second optical filament surface and applying a force for driving said filament in two opposing longitudinal directions whereby the distal end of the catheter is deflected.

* * * * *

UNITED STATES PATENT AND TRADEMARK OFFICE
CERTIFICATE OF CORRECTION

PATENT NO. : 4,899,732

DATED : February 13, 1990

INVENTOR(S) : Donald M. Cohen

It is certified that error appears in the above-identified patent and that said Letters Patent is hereby corrected as shown below:

Col. 3, line 52, delete "the circled" and insert -- a --

Col. 7, line 30, delete "3B" and insert -- 38 --

Signed and Sealed this

Sixteenth Day of June, 1992

Attest:

DOUGLAS B. COMER

*Attesting Officer*   Acting Commissioner of Patents and Trademarks